US010131607B2

(12) United States Patent
Dyballa et al.

(10) Patent No.: US 10,131,607 B2
(45) Date of Patent: Nov. 20, 2018

(54) PROCESS FOR PREPARING UNSYMMETRIC OCO PINCER LIGANDS FROM THE GROUP OF THE M-TERPHENYL COMPOUNDS (71) Applicant: EVONIK DEGUSSA GMBH, Essen (DE)

(72) Inventors: Katrin Marie Dyballa, Recklinghausen (DE); Robert Franke, Marl (DE); Dirk Fridag, Haltern am See (DE); Siegfried R. Waldvogel, Gau-Algesheim (DE); Bernd Elsler, Bonn (DE); Anton Wiebe, Neuwied (DE); Sebastian Lips, Hüffelsheim (DE)

(73) Assignee: EVONIK DEGUSSA GMBH, Essen (DE)

( * ) Notice: Subject to any disclaimer, the term of this patent is extended or adjusted under 35 U.S.C. 154(b) by 32 days.

(21) Appl. No.: 15/239,998

(22) Filed: Aug. 18, 2016

(65) Prior Publication Data
US 2017/0050910 A1 Feb. 23, 2017

(30) Foreign Application Priority Data

Aug. 21, 2015 (DE) .................. 10 2015 216 001

(51) Int. Cl.
*C07C 15/14* (2006.01)
*C07C 43/23* (2006.01)
*B01J 31/02* (2006.01)
*C25B 3/10* (2006.01)

(52) U.S. Cl.
CPC .......... *C07C 43/23* (2013.01); *B01J 31/0204* (2013.01); *C25B 3/10* (2013.01); *Y02P 20/55* (2015.11)

(58) Field of Classification Search
None
See application file for complete search history.

(56) References Cited

U.S. PATENT DOCUMENTS 8,747,646 B2 * 6/2014 Fischer .................... C25B 3/10
205/416

OTHER PUBLICATIONS

European Search Report for European Application No. 16 182787 dated Dec. 13, 2016 (2 pages).

Agapie, et al. Cyclometallated Tantalum Diphenolate Pincer Complexes: Intramolecular C—H/M—$CH_3$ Sigma-Bond Metathesis May Be Faster Than O—H/M—$CH_3$ Protonolysis. Organometallics 2007, 26. 2957-2959.
Agapie, et al. Cyclometallated Tantalum Diphenolate Pincer Complexes: Intramolecular C—H/M—$CH_3$ Sigma-Bond Metathesis May Be Faster Than O—H/M—$CH_3$ Protonolysis. May 3, 2007 (pp. 1-41).
Gruza, et al. Synthesis and Stereochemical Properties of "Extended" Biphenols Bridged by ortho-, meta- and para-Phenylene Spacers. European Journal of Organic Chemistry, 2009. 6318-6327.
Kirste, et al. Efficient Anodic and Direct Phenol-Arene C,C Cross-Coupling: The Benign Role of Water or Methanol. Journal of the American Chemical Society, 2012, 134, 3571-3576.
B.G. Pring. An Investigation of the Acid-catalyzed Demethylation and Dehydration of Some Tetramethoxyterphenyls. Acta Chem. Scand. 1973, 27, 3873-3880.
R. S. Grewal, H. Hart, T. K. Vinod. Oxacyclophanes Based on a m-Terphenyl Framework. J. Org. Chem. 1992, 57, 2721-2726.
S. Sarkar, A. R. Carlson, M. K. Veige, J. M. Falkowski, K. A. Abboud, A. S. Veige. Synthesis, Characterization, and Reactivity of a $d^2$, Mo(IV) Complex Supported by a New OCO-Trianionic Pincer Ligand. J. Am. Chem. Soc. 2008, 130, 1116-1117.
A. Kirste, B. Elsler, G. Schnakenburg, S. R. Waldvogel. Efficient Anodic and Direct Phenol-Arene C,C Cross-Coupling: The Benign Role of Water or Methanol. J. Am. Chem. Soc. 2012, 134, 3571-3576.
A. Kirste, S. Hayashi, G. Schnakenburg, I. M. Malkowsky, F. Stecker, A. Fischer, T. Fuchigami, S. R. Waldvogel. Highly Selective Electrosynthesis of Biphenols on Graphite Electrodes in Flourinated Media. Chem. Eur. J. 2011, 17, 14164-14169.
B. Elsler, D. Schollmeyer, K. M. Dyballa, R. Franke, S. R. Waldvogel. Metal- and Reagant-Free Highly Selective Anodic Cross-Coupling Reaction of Phenols. Angew. Chem. Int. Ed. 2014, 53, 5210-5213.
A. Kirste, M. Nieger, I. M. Malkowsky, F. Stecker, A. Fischer, S. R. Waldvogel, ortho-Selective Phenol-Coupling Reaction by Anodic Treatment on Boron-Doped Diamond Electrode Using Fluorinated Alcohols. Chem. Eur. J. 2009, 15, 2273-2277.

* cited by examiner

*Primary Examiner* — Ana Z Muresan
(74) *Attorney, Agent, or Firm* — Smith, Gambrell & Russell, LLP (57) ABSTRACT

The present invention relates to a process for preparing unsymmetric compounds from the group of the m-terphenyls which can be used as unsymmetric OCO pincer ligands, comprising the process steps of a) reacting a first substituted or unsubstituted phenol with a 1,3-disubstituted arene which may likewise be substituted in the 2 and 5 positions to obtain a phenol-arene coupling product and b) optionally protecting the OH group of the phenol-arene coupling product with a protecting group to obtain a protected phenol-arene coupling product, and c) reacting the phenol-arene coupling product from a) or b) with a second substituted or unsubstituted phenol to obtain an unsymmetric m-terphenyl, with the proviso that the first phenol and the second phenol have different substitution, characterized in that at least one of process steps a) and c) is conducted as an electrochemical process step.

24 Claims, 2 Drawing Sheets

PROCESS FOR PREPARING UNSYMMETRIC OCO PINCER LIGANDS FROM THE GROUP OF THE M-TERPHENYL COMPOUNDS

The present invention relates to a process for preparing unsymmetric compounds from the group of the m-terphenyls (hereinafter also called, as the case may be, m-terphenyl compounds or unsymmetric OCO pincer ligands), comprising the process steps of a) reacting a first substituted or unsubstituted phenol with a 1,3-disubstituted arene which may likewise be substituted in the 2 and 5 positions to obtain a phenol-arene coupling product and b) optionally protecting the OH group of the phenol-arene coupling product with a protecting group to obtain a protected phenol-arene coupling product, and c) reacting the phenol-arene coupling product from a) or b) with a second substituted or unsubstituted phenol to obtain an unsymmetric m-terphenyl, with the proviso that the first phenol and the second phenol have different substitution, characterized in that at least one of process steps a) and c) is conducted as an electrochemical process step.

m-Terphenyls is the name usually given to 1,3-diphenylbenzenes. Compounds from the group of the m-terphenyls consequently contain a characteristic 1,3-diphenylbenzene structure. In the context of the present invention, unsymmetric OCO pincer ligands are understood to mean compounds having a 1,3-diphenylbenzene unit where the two outer rings are not arenes but phenols. The OH groups of the two phenol units each have substitution ortho to the arene component.

Unsymmetric OCO pincer ligands are understood in the context of the present invention to mean compounds where the two phenols differ structurally, i.e. are different. In the context of the application, the arene component between the two different phenol components need not necessarily be symmetric; in other words, when a mirror plane is placed on the arene molecule, one side need not necessarily be an image of the other side.

In addition, in the context of the present invention, the following numbering is given to the positions in the arene component (B):

(B)

$R^9$ is defined as the substituent on carbon atom 1 in the benzene ring, $R^{10}$ as the substituent on carbon atom 2, $R^{11}$ as the substituent on carbon atom 3, $R^{12}$ as the substituent on carbon atom 5.

In the context of the present invention, substituted phenols are understood to mean those in which the hydrogen atoms on one or more ring carbon atoms have been replaced by substituents.

The conventional synthesis of OCO pincer ligands has to date been restricted to symmetric derivatives. The known processes enable $C_{Ar}$—$C_{Ar}$ bond formation, for example, via Ullmann coupling (B. G. Pring, *Acta Chem. Scand.* 1973, 27, 3873-3880), Grignard-Wurtz coupling (R. S. Grewal, H. Hart, T. K. Vinod, *J. Org. Chem.* 1992, 57, 2721-2726), or palladium-catalysed coupling reactions (S. Sarkar, A. R. Carlson, M. K. Veige, J. M. Falkowski, K. A. Abboud, A. S. Veige, *J. Am. Chem. Soc.* 2008, 130, 1116-1117). Before the actual coupling reactions, protection of the hydroxyl function is necessary, which in most cases is achieved by means of methylation. In all known cases, it is necessary to conduct the reaction with exclusion of moisture and under anaerobic conditions.

Scheme 1: State of the art for preparation of OCO pincer ligands (S. Sarkar, A. R. Carlson, M. K. Veige, J. M. Folkowski, K. A. Abbound, A. S. Veige, *J. Am. Chem. Soc.* 2008, 130, 1116-1117).

74%

(CDC')

as defined hereinafter.

A great disadvantage of the known methods for cross-coupling of phenol derivatives with arenes is the need for dry solvents and exclusion of air during the coupling reaction. In conventional cross-coupling methods, the protection of the hydroxyl functionality is necessary in most cases. In addition, for a regioselective cross-coupling, leaving functionalities which are introduced in the substrates used occur as environmentally problematic reaction wastes after the actual coupling reaction (see Scheme 1). Tolerance for functional groups is often restricted by the reagents used, and so usable derivatives are particularly those having a low degree of substitution. Toxic by-products (for example bromine compounds) often occur during the reaction, and have to be removed from the desired product in a complex manner and disposed of at great cost. Moreover, the reaction has to be conducted over very many stages, which is likewise very disadvantageous. Increasingly scarce raw materials make the preparation of ligand systems by palladium-catalysed cross-couplings or chemical oxidizing agents very costly.

The preparation of unsymmetric pincer ligands has not been possible to date by conventional methods. Nor are electrochemical methods for cross-coupling of phenols to give unsymmetric m-terphenyl compounds known to date.

The problem addressed by the present invention was therefore that of providing a simple process for preparing unsymmetric OCO pincer ligands from the group of the m-terphenyl compounds which avoids one or more disadvantages of the prior art.

It has been found that, surprisingly, this problem can be solved by conducting at least one of the process steps in a process having two process steps for the reaction as an electrochemical process step.

The present invention therefore provides a process for preparing unsymmetric compounds from the group of the m-terphenyls, called unsymmetric OCO pincer ligands, comprising the process steps of
a) reacting a first substituted or unsubstituted phenol with a 1,3-disubstituted arene which may likewise be substituted in the 2 and 5 positions to obtain a phenol-arene coupling product and
b) optionally protecting the OH group of the phenol-arene coupling product with a protecting group to obtain a protected phenol-arene coupling product,
c) reacting the phenol-arene coupling product from a) or b) with a second substituted or unsubstituted phenol to obtain an unsymmetric m-terphenyl,
with the proviso that the first phenol and the second phenol have different substitution, characterized in that
at least one of process steps a) and c) is conducted as an electrochemical process step.

The present invention likewise provides compounds of the formula (CDC')

The present invention also provides for the use of the compounds of the invention as ligand for preparation of metal-ligand catalyst systems.

The process of the invention has the advantage that the partial or complete conversion by means of electrochemical process steps significantly simplifies the preparation of unsymmetric m-terphenyl compounds, since exclusion of moisture or compliance with anaerobic reaction conditions need not be assured. This leads, inter alia, to a lower level of complexity in conducting the process.

The conduction of one or more process steps as electrochemical process steps also has the advantage that the formation of unwanted by-products can be distinctly reduced.

The electrochemical cross-coupling dispenses with the use of costly and toxic catalysts, and also the introduction of activating leaving functionalities prior to the phenol-arene coupling reaction (process step a) of the invention).

According to the way in which the process of the invention is executed, the process for the first time allows the direct synthesis of unsymmetric compounds with a low level of synthetic complexity and simultaneously high tolerance for functional groups in the substrates used.

Furthermore, in the process of the invention, it is possible to partly or preferably completely dispense with the use of chemical oxidizing agents. In this way, the risk of formation of by-products or contamination of the compounds by residues of the oxidizing agents is avoided.

The process of the invention also has the advantage that a great variety of different m-terphenyl compounds can be prepared, which were obtainable only at great cost and inconvenience, if at all, by the processes known from the prior art.

More particularly, the process of the invention has the advantage that the m-terphenyl compounds (m-terphenyls) of the invention can be prepared therewith.

The process according to the invention, the compounds according to the invention and the use thereof are described hereinafter by way of example, without any intention that the invention be restricted to these illustrative embodiments. When ranges, general formulae or compound classes are specified hereinbelow, these shall encompass not just the corresponding ranges or groups of compounds that are explicitly mentioned but also all subranges and subgroups of compounds obtainable by extracting individual values (ranges) or compounds. Where documents are cited in the context of the present description, their content shall fully form part of the disclosure content of the present invention, particularly in respect of the substantive matter in the context for which the document was cited. Where percent figures are given hereinafter, these are figures in % by volume unless stated otherwise. Where mean values are reported hereinafter, these are the numerical mean, unless stated otherwise. Where properties of a material are referred to hereinafter, for example viscosities or the like, these are properties of the material at 25° C., unless stated otherwise.

It is a feature of the process according to the invention for preparing unsymmetric compounds from the group of the m-terphenyls, comprising the process steps of a) reacting a first substituted or unsubstituted phenol with a 1,3-disubstituted arene which may likewise be substituted in the 2 and 5 positions to obtain a phenol-arene coupling product and b) optionally protecting the OH group of the phenol-arene coupling product with a protecting group to obtain a protected phenol-arene coupling product, and c) reacting the phenol-arene coupling product from a) or b) with a second substituted or unsubstituted phenol to obtain an unsymmetric m-terphenyl, with the proviso that the first phenol and the second phenol have different substitution, that at least one of process steps a) and c), preferably process step c), preferably both process steps a) and c), is conducted as an electrochemical process step.

Preferably, in the process according to the invention, substituted phenols are used both as the first phenol and as the second phenol.

It may be advantageous to isolate the phenol-arene coupling product from step a) before it is fed to process step c).

It is preferable in accordance with the invention to recover reactants unconverted in process steps a), b) and c), which is preferably effected by distillation. The reactants recovered can be fed back as starting material to the respective process steps a), b) and c).

Preferably, the electrochemical process step(s) is/are conducted in such a way that
aa) a mixture of at least one solvent and at least one conductive salt is produced,
bb) the compounds to be converted are added to this mixture, the substituted phenol (first or second substituted phenol) being added in molar deficiency relative to the other component to be converted (disubstituted arene or phenol-arene coupling product),
cc) at least two electrodes are introduced into the reaction solution obtained in bb) and a voltage is applied to the electrodes,
dd) the components are converted to the corresponding coupling product (phenol-arene or m-terphenyl coupling product),
ee) the voltage is switched off, and optionally
ff) the reaction product is isolated and/or purified.

If both process steps a) and c) are conducted as electrochemical process steps, the process of the invention is preferably conducted in such a way that it comprises the process steps of:
a1) mixing at least one solvent and a conductive salt,
a2) adding a first substituted or unsubstituted phenol and a 1,3-disubstituted arene which may likewise be substituted in the 2 and 5 positions to the mixture from a1), with addition of the 1,3-disubstituted arene in a molar excess relative to the first substituted or unsubstituted phenol,
a3) introducing at least two electrodes into the reaction solution and applying a voltage to the electrodes,
a4) coupling the first substituted or unsubstituted phenol to the 1,3-disubstituted arene to give a phenol-arene coupling product,
a5) switching off the voltage, removing and optionally purifying the phenol-arene coupling product,
b1) optionally protecting the OH group of the phenol-arene coupling product with a protecting group to obtain a protected phenol-arene coupling product and
c1) mixing the phenol-arene coupling product from step a5) or the protected phenol-arene coupling product from step b1) with a reaction solution composed of at least one solvent and a conductive salt present therein,
c2) adding a second substituted or unsubstituted phenol which has different substitution from the first substituted or unsubstituted phenol, the phenol-arene coupling product being present in a molar excess relative to the second substituted or unsubstituted phenol in the reaction solution,
c3) introducing at least two electrodes into the reaction solution and applying a voltage to the electrodes,
c4) coupling the second substituted or unsubstituted phenol to the phenol-arene coupling product to give an unsymmetric m-terphenyl,
c5) switching off the voltage and optionally
c6) isolating and/or working up the unsymmetric m-terphenyl.

The electrochemical process steps may be conducted, for example, in accordance with the processes for electrochemical coupling of carbon-carbon bonds described by a.) A. Kirste, B. Elsler, G. Schnakenburg, S. R. Waldvogel, *J. Am. Chem. Soc.* 2012, 134, 3571-3576, b.) A. Kirste, S. Hayashi, G. Schnakenburg, I. M. Malkowsky, F. Stecker, A. Fischer, T. Fuchigami, S. R. Waldvogel, *Chem. Eur. J.* 2011, 17, 14164-14169, c.) B. Elsler, D. Schollmeyer, K. M. Dyballa, R. Franke, S. R. Waldvogel, *Angew. Chem. Int. Ed.* 2014, 53, 5210-5213, and d.) A. Kirste, M. Nieger, I. M. Malkowsky, F. Stecker, A. Fischer, S. R. Waldvogel, *Chem. Eur. J.* 2009, 15, 2273-2277.

The electrochemical process steps can be conducted in all suitable electrolysis cells known from the prior art. Preference is given to using, in the process according to the invention, a flange cell, a beaker cell or a screening cell. Such cells are described in the literature, and the first two glass cells can be sourced, for example, under this name at HWS Labortechnik Mainz.

The cell has at least two electrodes. The electrodes used may be standard commercial electrodes. The anodes used may preferably, for example, be BDD (0.015 mm of boron-doped diamond on silicon or 0.05 mm of boron-doped diamond on niobium), or platinum, isostatic graphite or glassy carbon electrodes. The cathodes used are preferably BDD, nickel mesh or glassy carbon electrodes. Such BDD electrodes (boron-doped diamond on a support, for example niobium or silicon) are available, for example, under the DIACHEM name from Condias GmbH Itzehoe. The rest of the electrodes are available from standard chemical and material suppliers, for example Goodfellow or Aldrich.

The electrochemical process step(s) is/are preferably conducted in the presence of a solvent. The solvent used is preferably a solvent from the group of acetonitrile, propylene carbonate, methyl carbonate, nitromethane, ethylene glycol dimethyl ether, methanesulphonic acid, benzene, toluene, water, methanol, ethanol, propanol, isopropanol, halogenated solvents or halogenated or non-halogenated acids or mixtures thereof.

Solvents used are preferably a carboxylic acid, preferably formic acid, a fluorinated carboxylic acid or a fluorinated alcohol, preferably trifluoroacetic acid or 1,1,1,3,3,3-hexafluoro-2-propanol (HFIP), preferably 1,1,1,3,3,3-hexafluoro-2-propanol.

Particular preference is given to using, as solvents, methanol, formic acid, trifluoroacetic acid, hexafluoroisopropanol or mixtures thereof, preferably methanol, hexafluoroisopropanol or mixtures thereof, and more preferably hexafluoroisopropanol (1,1,1,3,3,3-hexafluoro-2-propanol).

The electrochemical process step(s) is/are preferably conducted in the presence of at least one conductive salt, the conductive salts used preferably being those selected from the group of tetra($C_1$-$C_6$-alkyl)ammonium and 1,3-di($C_1$-$C_6$-alkyl)imidazolium salts, with the proviso that the alkyl groups may be halogen-substituted, especially fluorine-substituted. Preference is given to using those conductive salts having counterions selected from the group comprising arsenate, sulphate, hydrogensulphate, alkylsulphate, alkylphosphate, perchlorate, fluoride, arylsulphate, hexafluorophosphate and tetrafluoroborate. Preferred conductive salts are those from the group of quaternary ammonium borates, ammonium fluoroalkylphosphates, ammonium fluoroalkylarsenates, ammonium trifluoromethylsulphonates, ammonium bis(fluoromethanesulphon)imides, ammonium tris (fluoromethanesulphonyl)methides, methyltributylammonium methylsulphate, methyltriethylammonium methylsulphate, tetrabutylammonium hexafluorophosphate, tetraethylammonium tetrafluoroborate, lithium hexafluorophosphate or tetraethylammonium tetrafluoroborate. Particular preference is given to using methyltriethylammonium methylsulphate or $Bu_3NMe^+MeOSO_3^-$ (methyltributylammonium methylsulphate), very particular preference to methyltributylammonium methylsulphate, as conductive salt.

The conductive salt is preferably used in a concentration of 0.001 to 10 mol/l, preferably 0.01 to 1 mol/l, more preferably from 0.075 to 0.125 mol/l and most preferably of 0.09 mol/l, based on the reaction mixture.

Preference is given to using, in the process according to the invention, at least a sufficient amount of first or second substituted phenol in each case that the concentration is from 0.001 to 5 mol/l, preferably from 0.05 to 0.5 mol/l, more preferably from 0.1 to 0.3 mol/l and especially preferably 0.15 mol/l.

The electrochemical process step(s) is/are preferably conducted at room temperature or elevated, temperature. Preferably, the electrochemical process step(s) is/are conducted at a temperature in the electrolysis cell in the range from 25 to 80° C., preferably from 35 to 70° C. and preferably from 45 to 55° C.

The electrochemical process step(s) is/are preferably conducted by galvanostatic means.

In the conduction of the electrochemical process step(s), the current is preferably chosen such that the current density is from 1 to 10 mA/cm$^2$, preferably from 2 to 5.5 mA/cm$^2$, preferably from 2.5 to 3 mA/cm$^2$ and more preferably 2.8 mA/cm$^2$. To conduct the electrochemical process step(s), preference is given to applying a (terminal) voltage between the electrodes in the range from 2 to 10 V, preferably 2.5 to 7.5 V and preferably from 3 to 6 V.

It may be advantageous when a sufficient amount of 1,3-disubstituted arene and first substituted or unsubstituted phenol is used such that the molar ratio of the 1,3-disubstituted arene to the first substituted or unsubstituted phenol is in the range from 1.5:1 to 6:1, preferably in the range of 2:1 to 3:1.

The molar ratio of the phenol-arene coupling product to the second substituted or unsubstituted phenol is preferably in the range from 1.5:1 to 6:1, preferably in the range from 2:1 to 3:1.

Particular preference is given to choosing the quantity ratios such that, in step a), the molar ratio of the 1,3-disubstituted arene to the first substituted or unsubstituted phenol is in the range from 1.5:1 to 6:1, preferably in the range of 2:1 to 3:1, and, in step b), the molar ratio of the phenol-arene coupling product to the second substituted or unsubstituted phenol is in the range from 1.5:1 to 6:1, preferably in the range from 2:1 to 3:1.

In the process according to the invention, first substituted or unsubstituted phenols used are preferably those of the formula (A)

(A)

second substituted or unsubstituted phenols used are preferably those of the formula (A')

(A')

and 1,3-disubstituted arenes which may likewise be substituted in the 2 and 5 positions that are used are preferably those of the formula (B)

(B)

in which the radicals
$R^1$, $R^2$, $R^3$, $R^4$, $R^5$, $R^6$, $R^7$, $R^8$, $R^{10}$ and $R^{12}$ are each independently selected from the group consisting of hydrogen, ($C_1$-$C_{12}$)-alkyl, O—($C_1$-$C_{12}$)-alkyl, ($C_6$-$C_{20}$)-aryl, O—($C_6$-$C_{20}$)-aryl and halogen, preferably consisting of hydrogen, ($C_1$-$C_{12}$)-alkyl, O—($C_1$-$C_{12}$)-alkyl and halogen, more preferably consisting of hydrogen, ($C_1$-$C_{12}$)-alkyl, O—($C_1$-$C_{12}$)-alkyl,
in which $R^9$ and $R^{11}$ are each independently selected from the group consisting of ($C_1$-$C_{12}$)-alkyl, O—($C_1$-$C_{12}$)-alkyl, ($C_6$-$C_{20}$)-aryl, O—($C_6$-$C_{20}$)-aryl and halogen, preferably consisting of ($C_1$-$C_{12}$)-alkyl, O—($C_1$-$C_{12}$)-alkyl and halogen, more preferably consisting of ($C_1$-$C_{12}$)-alkyl, O—($C_1$-$C_{12}$)-alkyl,
and in which at least one pair among the $R^1/R^5$, $R^2/R^6$, $R^3/R^7$ and $R^4/R^8$ pairs consists of different radicals.

In the context of the present invention, halogen is understood to mean fluorine, chlorine, bromine or iodine, especially fluorine, chlorine and bromine. The term "alkyl" in the context of the present invention is understood to mean a linear or branched hydrocarbon radical in which one or more hydrogen atoms may optionally be replaced, preferably by halogen atoms or hydroxyl or alk(yl)oxy groups. Aryl in the context of the present invention means aromatic hydrocarbyl radicals, for example phenyl-($C_6H_5$—), naphthyl-($C_{10}H_7$—), anthryl-($C_{14}H_9$—), preferably phenyl, in which one or more hydrogen atoms may optionally be replaced, preferably by alkyl or alk(yl)oxy groups.

In the context of the invention, the expression "—($C_1$-$C_{12}$)-alkyl" encompasses straight-chain and branched alkyl groups. Preferably, these groups are unsubstituted straight-chain or branched —($C_1$-$C_5$)-alkyl groups and most preferably —($C_1$-$C_6$)-alkyl groups. Examples of —($C_1$-$C_{12}$)-alkyl groups are especially methyl, ethyl, propyl, isopropyl, n-butyl, isobutyl, sec-butyl, tert-butyl, n-pentyl, 2-pentyl, 2-methylbutyl-, 3-methylbutyl-, 1,2-dimethylpropyl-, 1,1-dimethylpropyl, 2,2-dimethylpropyl-, 1-ethylpropyl-, n-hexyl-, 2-hexyl-, 2-methylpentyl-, 3-methylpentyl-, 4-methylpentyl-, 1,1-dimethylbutyl-, 1,2-dimethylbutyl-, 2,2-dimethylbutyl-, 1,3-dimethylbutyl-, 2,3-dimethylbutyl-, 3,3-dimethylbutyl-, 1,1,2-trimethylpropyl-, 1,2,2-trimethylpropyl-, 1-ethylbutyl-, 1-ethyl-2-methylpropyl-, n-heptyl-, 2-heptyl-, 3-heptyl-, 2-ethylpentyl-, 1-propylbutyl-, n-octyl-, 2-ethylhexyl-, 2-propylheptyl-, nonyl-, decyl- and dodecyl-.

The "($C_1$-$C_{12}$)-alkyl and O—($C_1$-$C_{12}$)-alkyl" radicals may each be unsubstituted or substituted by one or more identical or different radicals selected from ($C_3$-$C_{12}$)-cycloalkyl, ($C_3$-$C_{12}$)-heterocycloalkyl, ($C_6$-$C_{20}$)-aryl, fluorine, chlorine, cyano, formyl, acyl and alkoxycarbonyl.

The elucidations relating to the expression "—($C_1$-$C_{12}$)-alkyl" also apply to the alkyl groups in —O—($C_1$-$C_{12}$)-alkyl, i.e. in —($C_1$-$C_{12}$)-alkoxy. Preferably, these groups are unsubstituted straight-chain or branched —($C_1$-$C_6$)-alkoxy groups.

In the context of the present invention, the expression "—($C_6$-$C_{20}$)-aryl" encompasses mono- or polycyclic aromatic hydrocarbyl radicals. These have 6 to 20 ring atoms, more preferably 6 to 14 ring atoms, especially 6 to 10 ring atoms. Aryl is preferably —($C_6$-$C_{10}$)-aryl and —($C_6$-$C_{10}$)-aryl-($C_6$-$C_{10}$)-aryl-. Aryl is especially phenyl, naphthyl, indenyl, fluorenyl, anthracenyl, phenanthrenyl, naphthacenyl, chrysenyl, pyrenyl, coronenyl. More particularly, aryl is phenyl, naphthyl and anthracenyl.

Substituted —($C_6$-$C_{20}$)-aryl groups may have one or more (e.g. 1, 2, 3, 4 or 5) substituents, depending on the ring size. These substituents are preferably each independently selected from —H, —($C_1$-$C_{12}$)-alkyl, —O—($C_1$-$C_{12}$)-alkyl, —O—($C_6$-$C_{20}$)-aryl, —($C_6$-$C_{20}$)-aryl, -halogen (such as Cl, F, Br, I), —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —$SO_3H$, —$SO_3Na$, —$NO_2$, —CN, —$NH_2$, —N[($C_1$-$C_{12}$)-alkyl].

The conduct of the process of the invention is shown by way of example hereinafter by two reaction schemes, with both process steps a) and c) being conducted here as electrochemical process steps. The $R^1$ to $R^{12}$ radicals used in the schemes are as defined above. The coupling of a substituted or unsubstituted phenol to a 1,3-disubstituted arene which may likewise be substituted in the 2 and 5 positions in the first process step a) (Scheme 2) leads to the phenol-arene coupling product (AB).

Scheme 2: Process step a)

In the second process step c), the phenol-arene coupling product (AB) is reacted with a further substituted or unsubstituted phenol (A') to give the compound ABA' and thus converted to an unsymmetric OCO pincer ligand (Scheme 3).

Scheme 3: Process step c)

Such compounds have not been described to date by a conventional route or are obtainable only with a high level of synthetic complexity.

It may be advantageous when a process step b) in which the hydroxyl group of the phenol-arene coupling product is protected by a suitable protecting group is conducted between process step a) and process step c). Such a process step is advantageous especially when the two process steps a) and c) are conducted as electrochemical process steps.

In one variant of the process according to the invention, what are therefore used in process step c) are protected phenol-arene coupling products, preferably those of the formula (A″B)

(A″B)

together with the second substituted or unsubstituted phenol, preferably one of the formula (A′)

(A′)

in which X=—OR′, with R′=a protecting group, preferably a silyl protecting group, preferably a -trimethylsilyl, -triethylsilyl, -triisopropylsilyl, -tert.-butyldiphenylsilyl or (1,1-dimethylethyl)dimethylsilyl protecting group, more preferably a -triisopropylsilyl- or (1,1-dimethylethyl)dimethylsilyl protecting group, and $R^1$, $R^2$, $R^3$, $R^4$, $R^5$, $R^6$, $R^7$, $R^8$, $R^{10}$ and $R^{12}$ are each independently selected from the group comprising hydrogen, $(C_1-C_{12})$-alkyl, O—$(C_1-C_{12})$-alkyl, $(C_6-C_{20})$-aryl, O—$(C_6-C_{20})$-aryl and halogen, preferably consisting of hydrogen, $(C_1-C_{12})$-alkyl, O—$(C_1-C_{12})$-alkyl and halogen, more preferably consisting of hydrogen, $(C_1-C_{12})$-alkyl, O—$(C_1-C_{12})$-alkyl, in which the $R^9$ and $R^{11}$ radicals are each independently selected from the group consisting of $(C_1-C_{12})$-alkyl, O—$(C_1-C_{12})$-alkyl, $(C_6-C_{20})$-aryl, O—$(C_6-C_{20})$-aryl and halogen, preferably consisting of $(C_1-C_{12})$-alkyl, O—$(C_1-C_{12})$-alkyl and halogen, more preferably consisting of $(C_1-C_{12})$-alkyl, O—$(C_1-C_{12})$-alkyl,
and
in which at least one pair among the $R^1/R^5$, $R^2/R^6$, $R^3/R^7$ or $R^4/R^8$ pairs consists of different radicals.

Process step b) can be conducted in such a way that the phenol-arene coupling product from process step a) is reacted with a suitable compound before or after a workup. Preference is given to inserting a silyl protecting group. Particular preference is given to using, as the compound, (1,1-dimethylethyl)dimethylsilyl chloride and tri(methylethyl)silyl chloride.

Silyl protecting groups and the introduction thereof are known to those skilled in the art and can be found in the standard technical literature (in this regard, see also: P. G. M. Wuts, T. W. Greene "Greene's Protective Groups in Organic Synthesis", fourth edition, 2007, John Wiley and Sons; Hoboken, N.J.).

The inventors have found that, surprisingly, in the case of use of a phenol-arene coupling product having a protected hydroxyl group, especially a hydroxyl group protected by reaction with a silyl group, in process step c), when it is conducted as an electrochemical process step, the protecting group is eliminated again, such that an m-terphenyl compound again having two OH groups is obtained.

The inventors have also found that, surprisingly, through the introduction of a protecting group, especially a silyl group, into the phenol-arene coupling product in the subsequent coupling in process step c) conducted by electrochemical means, it is possible to increase the yield of m-terphenyl compound again having two OH groups. Thus, it is possible to once again distinctly improve the efficiency of the overall process.

The process of the invention is preferably conducted in such a way that the reaction in the electrochemical process steps, preferably the entire reaction, is conducted without the use of organic oxidizing agents.

With the aid of the process of the invention, it is possible to prepare a great variety of different m-terphenyl compounds, especially those of the formula (ABA′)

(ABA′)

with X, Y and $R^1$ to $R^{12}$ as defined above. With the process of the invention, it is especially possible to prepare the inventive compounds of the formula (CDC′). The inventive compounds of the formula (CDC′)

(CDC′)

in which the $R^{13}$, $R^{14}$, $R^{15}$, $R^{16}$, $R^{19}$, $R^{20}$, $R^{21}$ and $R^{22}$ radicals are each independently selected from the group consisting of hydrogen, $(C_1-C_{12})$-alkyl, O—$(C_1-C_{12})$-alkyl, $(C_6-C_{20})$-aryl, O—$(C_6-C_{20})$-aryl, halogen, preferably consisting of hydrogen, $(C_1-C_{12})$-alkyl, O—$(C_1-C_{12})$-alkyl, halogen, more preferably consisting of hydrogen, $(C_1-C_{12})$-alkyl and O—$(C_1-C_{12})$-alkyl,
in which $R^{17}$ and $R^{18}$ are each independently selected from the group consisting of $(C_1-C_{12})$-alkyl, O—$(C_1-C_{12})$-alkyl, $(C_6-C_{20})$-aryl, O—$(C_6-C_{20})$-aryl and halogen, preferably consisting of $(C_1-C_{12})$-alkyl, $O-(C_1-C_{12})$-alkyl and halogen, more preferably consisting of $(C_1-C_{12})$-alkyl and $O-(C_1-C_{12})$-alkyl, and in which at least one pair among the $R^{13}/R^{22}$, $R^{14}/R^{21}$, $R^{15}/R^{20}$ or $R^{16}/R^{19}$ pairs consists of different radicals.

Preferably, the $R^{13}$, $R^{14}$, $R^{15}$, $R^{16}$, $R^{19}$, $R^{20}$, $R^{21}$ and $R^{22}$ radicals are each independently selected from the group consisting of hydrogen, $(C_1-C_{12})$-alkyl, $O-(C_1-C_{12})$-alkyl, halogen, and the $R^{17}$ and $R^{18}$ radicals are each independently selected from the group consisting of $(C_1-C_{12})$-alkyl, $O-(C_1-C_{12})$-alkyl or halogen.

More preferably, the $R^{13}$, $R^{14}$, $R^{15}$, $R^{16}$, $R^{19}$, $R^{20}$, $R^{21}$ and $R^{22}$ radicals are each independently selected from the group consisting of hydrogen, $(C_1-C_{12})$-alkyl, $O-(C_1-C_{12})$-alkyl, and the $R^{17}$ and $R^{18}$ radicals are each independently selected from the group consisting of $(C_1-C_{12})$-alkyl, $O-(C_1-C_{12})$-alkyl.

Very particularly preferred compounds according to the invention are those that satisfy the formula (1), (2) or (3)

The compounds of the invention can be used as ligand for preparation of metal-ligand catalyst systems.

The present invention is described by way of example with reference to FIGS. 1 to 4, without any intention that the invention, the scope of application of which is apparent from the overall description and the claims, be restricted to the embodiments depicted in the figures. FIGS. 1 to 4 depict schematic drawings of cells as are usable in the process according to the invention, and as used particularly in the examples which follow.

FIG. 2 shows a schematic of a flange cell (glass). Indicated in FIG. 2 are a stainless steel rod with a secured nickel mesh cathode (1), a Teflon stopper (2), a cooling jacket (glass) (3), a screw clamp (4), a BDD electrode (5), an EPDM seal (6) and a stirrer magnet (7).

FIG. 3 shows a schematic of a small beaker cell (glass). Indicated in FIG. 3 are a stainless steel rod for forming contacts (1), a Teflon stopper (2), a cell outlet/connection (3), for example for a Dimroth condenser, electrode holders (stainless steel) (4), glassy carbon electrodes (5) and a stirrer magnet (6).

FIG. 4 shows a schematic of a large beaker cell (glass). Indicated in FIG. 4 are BDD electrodes (1), the connections for forming contacts (2), the glass shell (3), a stirrer magnet (4), a cell outlet/connection (5), for example for a Dimroth condenser, and an electrically conductive contact (stainless steel foil) (6).

Figure 1:
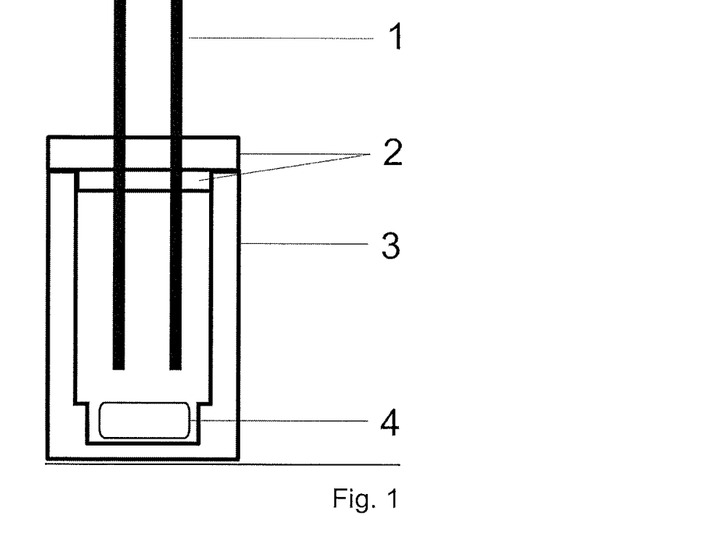
FIG. 1 shows a schematic of a screening cell. Indicated in FIG. 2 are the BDD electrodes (1), a Teflon lid (2), a Teflon beaker (3) and a stirrer magnet (4).
Figure 2:
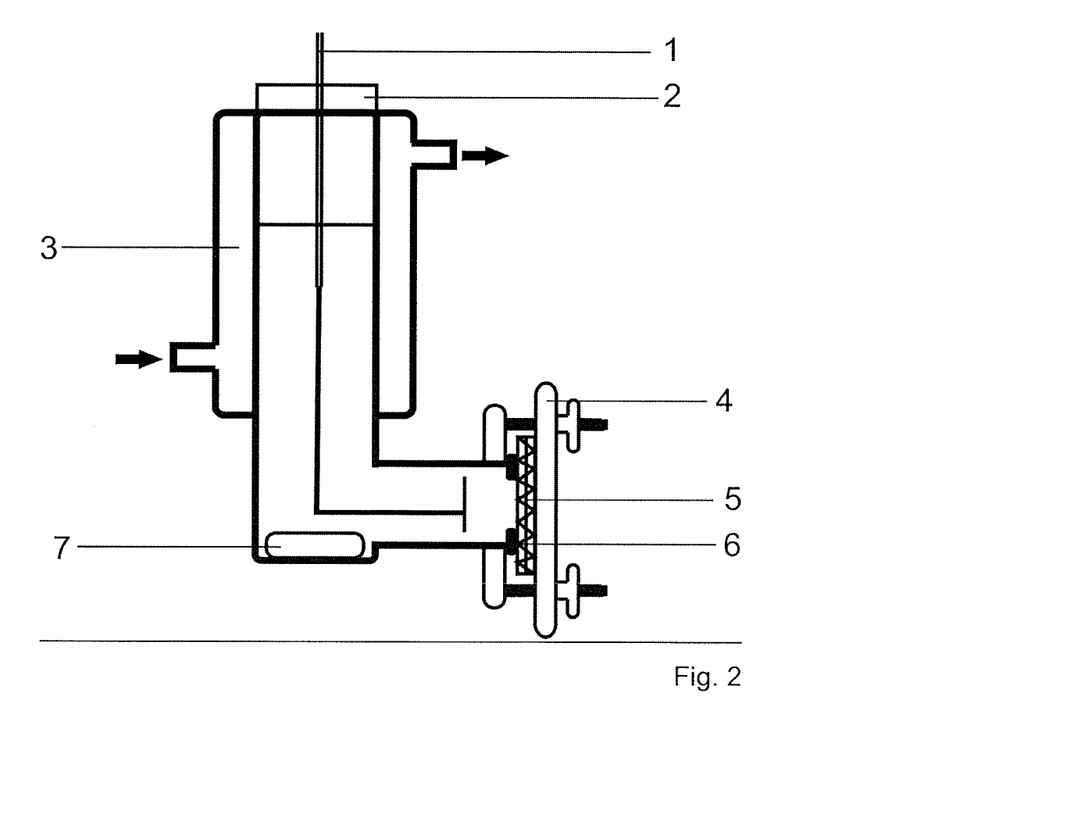
Figure 3:
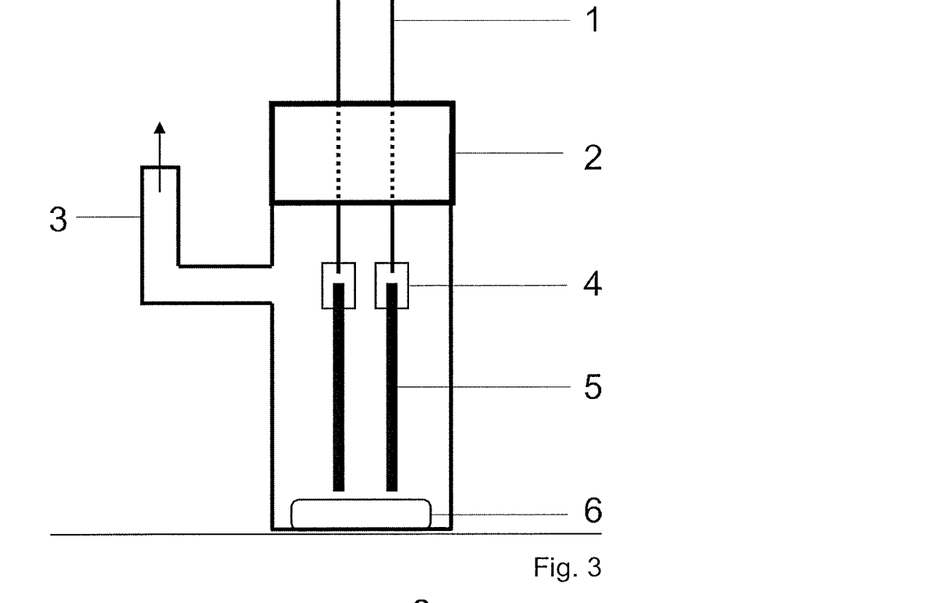
Figure 4:
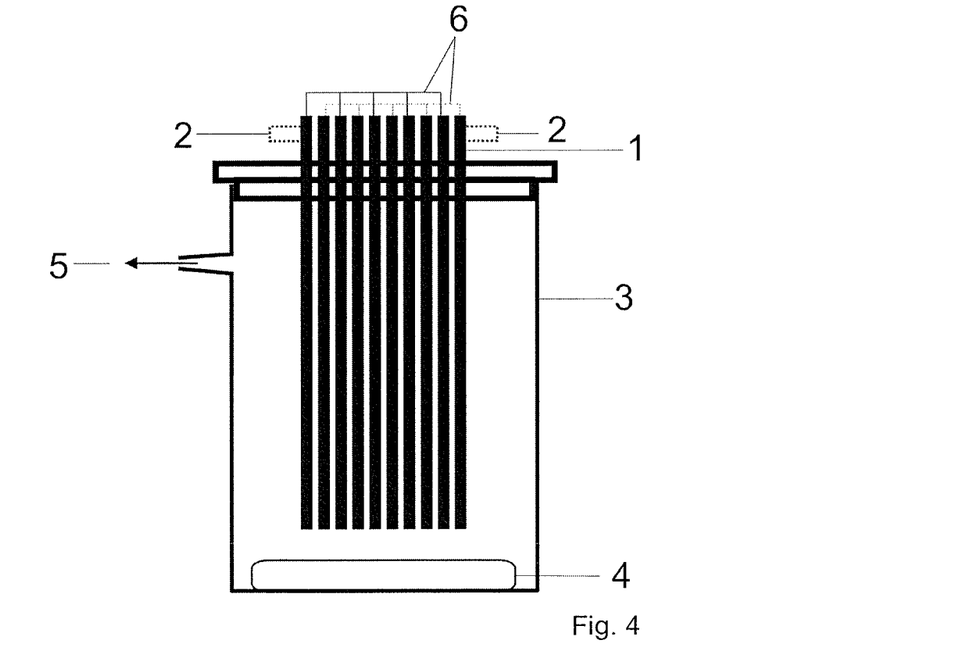

The examples adduced below illustrate the present invention by way of example, without any intention that the invention, the scope of application of which is apparent from the entirety of the description and the claims, be restricted to the embodiments specified in the examples.

EXPERIMENTAL

General Methods

Chromatography (GC/GCMS)

Preparative liquid chromatography for separation of substance mixtures was conducted using 60 M silica gel (0.040-0.063 mm) from MACHERY-NAGEL GMBH & CO. KG, Duren at a maximum pressure of 2 bar. All the eluents used (ethyl acetate, technical grade quality; cyclohexane, technical grade quality) were purified beforehand by distillation on a rotary evaporator.

Thin-layer chromatography (TLC) was conducted on ready-made PSC silica gel 60 $F_{254}$ plates from Merck KGaA, Darmstadt. The various substances were detected first under UV light and then by staining by means of cerium-molybdophosphoric acid reagent (5.6 g of molybdophosphoric acid, 2.2 g of cerium(IV) sulphate tetrahydrate and 13.3 g of conc. sulphuric acid in 200 ml of water), followed by heating with a hot air gun.

Gas Chromatography (GC/GCMS)

The gas chromatography studies (GC) on product mixtures and pure substances were effected with the aid of the GC-2010 gas chromatograph from Shimadzu, Japan. Analysis is effected on an HP-5 quartz capillary column from Agilent Technologies, USA (length: 30 m; internal diameter: 0.25 mm; film thickness of the covalently bound stationary phase: 0.25 µm; carrier gas: hydrogen; injector temperature: 250° C.; detector temperature: 310° C.; programme: "hard" method: start temperature 50° C. for 1 min, heating rate: 15° C./min, end temperature 290° C. for 8 min). Gas chromatography-mass spectra (GCMS) of product mixtures and pure substances were recorded with the aid of the GC-2010 gas chromatograph combined with the GCMS-QP2010 mass detector from Shimadzu, Japan. Analysis is effected on an HP-1 quartz capillary column from Agilent Technologies, USA (length: 30 m; internal diameter: 0.25 mm; film thickness of the covalently bound stationary phase: 0.25 µm; carrier gas: hydrogen; injector temperature: 250° C.; detector temperature: 310° C.; programme: "hard" method: start temperature 50° C. for 1 min, heating rate: 15° C./min, end temperature 290° C. for 8 min; GC-MS: ion source temperature: 200° C.).

Mass Spectrometry

All electrospray ionization analyses (ESI+) were conducted on a QT of Ultima 3 from Waters Micromasses, Milford, Mass. EI mass spectra and the high-resolution EI spectra were analysed on an instrument of the MAT 95 XL sector field instrument type from Thermo Finnigan, Bremen.

NMR Spectroscopy

The NMR spectroscopy studies were conducted on multinucleus resonance spectrometers of the AC 300 or AV II 400 type from Bruker, Analytische Messtechnik, Karlsruhe. The solvent used was CDCl3. The $^1$H and $^{13}$C spectra were calibrated according to the residual content of undeuterated solvent using the NMR Solvent Data Chart from Cambridge Isotopes Laboratories, USA. Some of the $^1$H and $^{13}$C signals were assigned with the aid of H,H-COSY, H,H-NOESY, H,C-HSQC and H,C-HMBC spectra. The chemical shifts are reported as δ values in ppm. For the multiplicities of the NMR signals, the following abbreviations were used: s (singlet), bs (broad singlet), d (doublet), t (triplet), q (quartet), m (multiplet), dd (doublet of doublets), dt (doublet of triplets), tq (triplet of quartets). All coupling constants J were reported in hertz (Hz) together with the number of bonds covered. The numbering given in the assignment of signals corresponds to the numbering shown in the formula schemes, which need not necessarily correspond to IUPAC nomenclature.

Single Crystal Structure Analyses

The single crystal structure analyses were conducted in the Institute of Organic Chemistry at the Johannes Gutenberg University of Mainz on an IPDS 2T instrument from STOE & Cie GmbH, Darmstadt.

Melting Points

The relevant melting points were measured with the aid of the SG 2000 melting point determination instrument from HW5, Mainz, and were adopted in uncorrected form.

General Procedures

GP1

Electrochemical Cross-Coupling in L Cells 5 mmol of the species A or A' to be oxidized (deficiency component) were reacted with a 2-3-fold excess (10-15 mmol) of the coupling partner B or AB in 33 ml of 1,1,1,3,3,3-hexafluoroisopropanol (HFIP) or 33 ml of (HFIP with 18% by volume of methanol (MeOH) based on the sum total of HFIP and MeOH) in an undivided flange cell with a BDD anode and nickel mesh cathode. The conductive salt used was $Bu_3NMe^+MeOSO_3^-$ (MTBS) with a concentration of 0.09 M. The electrolysis was galvanostatic. The outer shell of the electrolysis cell was kept at a controlled temperature of about 10° C. by means of a thermostat, while the reaction mixture was stirred and heated to 50° C. with the aid of an oil bath. After the electrolysis had ended, the cell contents were transferred to a 50 ml round-bottom flask and the solvent was removed under reduced pressure on a rotary evaporator at 50° C., 200-70 mbar. Mineralization products and the conductive salt present were separated by elution by means of ethyl acetate (300 ml) using 50 g of silica gel 60. Unconverted reactant was recovered by means of short-path distillation in a Kugelrohr still (100° C., $10^{-3}$ mbar). The reaction products formed were separated by column chromatography as specified in each case.

Electrode Material:
    Anode: BDD (15 µm diamond layer) on silicon support
    Cathode: nickel mesh
Electrolysis Conditions:
    Temperature: 50° C.
    Current density: 2.8 mA/cm$^2$
    Charge: 2-4 F based on the deficiency component
    Terminal voltage: 3-6 V

GP2

Electrochemical Cross-Coupling in a Beaker Cell with Stacked Electrode Arrangement 120 mmol of the species A to be oxidized (deficiency component) were reacted with a 2-3-fold excess (240-360 mmol) of the coupling partner B in 750 ml of 1,1,1,3,3,3-hexafluoroisopropanol or 750 ml of (HFIP with 18% by volume of MeOH, based on the sum total of HFIP and MeOH) in a beaker cell with a stacked arrangement of 10 BDD electrodes (5×anode, 5×cathode). The conductive salt used was MTBS with a concentration of 0.09 M. The electrolysis was galvanostatic. Evaporating HFIP was redistilled with the aid of a Dimroth condenser and fed to the electrolysis, while the reaction mixture was stirred and heated to 50° C. with the aid of an oil bath. After the electrolysis had ended, the cell contents were transferred to a 1 l round-bottom flask and the solvent was removed under reduced pressure on a rotary evaporator at 50° C., 200-70 mbar. Mineralization products and the conductive salt present were removed by elution by means of ethyl acetate (2 l) using 300 g of silica gel 60. Unconverted reactant was recovered by means of short-path distillation in a Kugelrohr still (100° C., $10^{-3}$ mbar).

Electrode material:
    Anode: 5×BDD on niobium
    Cathode: 5×BDD on niobium
Electrolysis conditions:
    Temperature: 50° C.
    Current density: 2.8 mA/cm$^2$
    Charge: 2-4 F based on the deficiency component
    Terminal voltage: 3-6 V

GP3

Electrochemical Cross-Coupling in a Beaker Cell 3.8 mmol of the species A to be oxidized (deficiency component) were reacted with a 2-3-fold excess (7.6-11 mmol) of the coupling partner B in 25 ml of 1,1,1,3,3,3-hexafluoroisopropanol or 25 ml of (HFIP with 18% by volume of MeOH, based on the sum total of HFIP and MeOH) in a beaker cell on glassy carbon electrodes. The conductive salt used was MTBS with a concentration of 0.09 M. The electrolysis was galvanostatic. Evaporating HFIP was redistilled with the aid of a Dimroth condenser and fed to the electrolysis, while the reaction mixture was stirred and heated to 50° C. with the aid of an oil bath. After the electrolysis had ended, the cell contents were transferred to a 100 ml round-bottom flask and the solvent was removed under reduced pressure on a rotary evaporator at 50° C., 200-70 mbar. Mineralization products and the conductive salt present were removed by elution by means of ethyl acetate (300 ml) using 50 g of silica gel 60. Unconverted reactant was recovered by means of short-path distillation in a Kugelrohr still (100° C., $10^{-3}$ mbar).

Electrode material:
  Anode: glassy carbon
  Cathode: glassy carbon
Electrolysis conditions:
  Temperature: 50° C.
  Current density: 2.8 mA/cm$^2$
  Charge: 2-4 F based on the deficiency component
  Terminal voltage: 3-6 V

GP4

Electrochemical Cross-Coupling in a Screening Cell 0.76 mmol of the species A to be oxidized (deficiency component) were reacted with a 2-3-fold excess (1.52-2.28 mmol) of the coupling partner B in 5 ml of 1,1,1,3,3,3-hexafluoroisopropanol or 5 ml of (HFIP with 18% by volume of MeOH, based on the sum total of HFIP and MeOH) in a beaker cell on glassy carbon electrodes. The conductive salt used was MTBS with a concentration of 0.09 M. The electrolysis was galvanostatic. The reaction mixture was placed in a stainless steel block, stirred with the aid of a heated stirrer and kept at 50° C. After the electrolysis had ended, the cell contents were transferred to a 50 ml round-bottom flask and the solvent was removed under reduced pressure on a rotary evaporator at 50° C., 200-70 mbar. Mineralization products and the conductive salt present were removed by elution by means of ethyl acetate (150 ml) using 20 g of silica gel 60. Unconverted reactant was recovered by means of short-path distillation in a Kugelrohr still (100° C., $10^{-3}$ mbar).

Electrode material:
  Anode: BDD (50 μm) on niobium
  Cathode: BDD (50 μm) on niobium
Electrolysis conditions:
  Temperature: 50° C.
  Current density: 2.8 mA/cm$^2$
  Charge: 2-4 F based on the deficiency component
  Terminal voltage: 3-6 V

Two-Stage Pincer Ligand Synthesis

Example 1

3,4'-Dimethoxy-2',5-dimethyl-2-hydroxybiphenyl and 2',3-dimethoxy-4',5-dimethyl-2-hydroxybiphenyl

The electrolysis was conducted according to GP1, except that 1.45 g (10.5 mmol, 2.0 equiv.) of 4-methylguaiacol and 639 mg (5.23 mmol, 1.0 equiv.) of 3-methylanisole were used. The current density was 2.8 mA/cm$^2$, the charge 4 F per 3-methylanisole (Q=2018 C). After removal of the solvent, the product mixture was purified by column chromatography on silica gel 60 with an eluent of volume ratio 9:1 (CH (cyclohexane):EA (ethyl acetate)). The products were obtained as yellowish oily substances.

3,4'-Dimethoxy-2',5-dimethyl-2-hydroxybiphenyl

Yield: 206 mg (0.8 mmol, 15%)
GC (hard method, HP-5): $t_R$=13.45 min
$R_f$(Cy:EA=4:1)=0.44
$^1$H NMR (400 MHz, CDCl$_3$) δ [ppm]=2.20 (s, 3H, H-9), 2.32 (2, 3H, H-8), 3.83 (s, 3H, H-10), 3.92 (s, 3H, H-7), 5.44 (bs, 1H, H-11), 6.57 (m, 1H, H-4, $^4J_{4,6}$=1.8 Hz), 6.70 (dd, 1H, H-6, $^4J_{4,6}$=1.8 Hz), 6.78-6.82 (dd, 1H, H-5', $^4J_{3',5'}$=2.7 Hz, $^4J_{2',3'}$,=8.3 Hz), 6.84 (d, 1H, H-3', $^4J_{3',5'}$=2.7 Hz), 7.15 (d, 1H, H-6', $^4J_{2',3}$=8.3 Hz).
$^{13}$C NMR (101 MHz, CDCl$_3$) δ [ppm]=21.14 (C-8), 21.57 (C-9), 55.86 (C-10), 55.95 (C-7), 110.73 (C-5'), 111.21 (C-4), 112.17 (C-3'), 121.85 (C-6), 123.53 (C-1), 125.38 (C-6'), 129.09 (C-5), 131.53 (C-1'), 139.08 (C-2'), 140.93 (C-2), 147.25 (C-3), 155.98 (C-4').
HRMS (ESI, pos. mode): m/z for C$_{16}$H$_{19}$O$_3$[M+H$^+$]: calculated: 259.1334. found: 259.1332.

2',3-Dimethoxy-4',5-dimethyl-2-hydroxybiphenyl

Yield: 225 mg (0.88 mmol, 17%)
GC (hard method, HP-5): $t_R$=13.32 min
$R_f$(Cy:EA=4:1)=0.57
$^1$H NMR (400 MHz, CDCl$_3$) δ [ppm]=2.33 (s, 3H, H-10), 2.41 (s, 3H, H-8), 3.84 (s, 3H, H-9), 3.91 (s, 3H, H-7), 5.86 (bs, 1H, H-11), 6.68 (m, 1H, H-6'), 6.71 (d, 1H, H-4, $^4J_{4,6}$=1.7 Hz), 6.84 (m, 1H, H-3'), 6.86-6.90 (m, 1H, H-5'), 7.19-7.22 (d, 1H, H-6', $^3J_{5',6}$=7.6 Hz).
$^{13}$C NMR (101 MHz, CDCl$_3$) δ [ppm]=21.14 (C-8), 21.56 (C-10), 55.87 (C-7), 55.95 (C-9), 111.21 (C-1), 112.17 (C-3'), 121.85 (C-4), 123.53 (C-1'), 123.99 (C-5'), 125.38 (C-6'), 129.09 (C-5), 131.53 (C-6), 139.08 (C-4'), 140.86 (C-2), 147.26 (C-3), 155.98 (C-2').
HRMS (ESI, pos. mode): m/z for C$_{16}$H$_{18}$O$_3$Na [M+Na$^+$]: calculated: 281.1154. found: 281.1165.

Example 2

2-Hydroxy-5-methyl-2',3,4'-trimethoxybiphenyl

The electrolysis was conducted according to GP2 with 16.58 g (120 mmol, 1.0 equiv.) of 4-methylguaiacol and 49.74 mg (360 mmol, 3.0 equiv.) of 1,3-dimethoxybenzene. The current density was 2.8 mA/cm², the charge 2 F per 4-methylguaiacol (Q=23156 C). After removal of the solvent and the conductive salt, the product was obtained by short-path distillation in a Kugelrohr still as a yellow oil (140° C., $10^{-3}$ mbar).

Yield: 9.218 g (33.6 mmol; 28%)
GC (hard method, HP-5): $t_R$=14.27 min
$R_f$(Cy:EA=9:1)=0.42
$^1$H NMR (400 MHz, CDCl$_3$) δ [ppm]=2.33 (s, 3H, 9-H), 3.83 (s, 3H, 8-H), 3.85 (s, 3H, 10-H), 3.91 (s, 3H, 11-H), 5.76 (bs, 1H, 7-H), 6.59-6.61 (m, 2H, 5'-H, 6'-H), 6.67 (s, 1H, 6-H), 6.70 (s, 1H, 4-H), 7.23 (s, 1H, 3'-H).
$^{13}$C NMR (101 MHz, CDCl$_3$) δ [ppm]=21.29 (C-7), 55.56 (C-10), 56.02 (C-9), 56.11 (C-8), 99.12, 105.19 (C-5', C-6'), 111.22 (C-4), 119.65 (C-1'), 123.83 (C-6), 125.18 (C-1), 129.14 (C-5), 132.30 (C-3'), 141.04 (C-2), 147.28 (C-3), 157.40 (C-2'), 160.68 (C-4').
HRMS (ESI, pos. mode): m/z for C$_{16}$H$_{18}$O$_4$(M+Na$^+$): calculated: 297.1103. found: 297.1096.

Example 3

2,2''-Dihydroxy-5'',2'-dimethyl-3-(1,1-dimethylethyl)-3'',4',5-trimethoxy[1,1';5',1'']terphenyl The electrolysis was conducted according to GP1 with 325 mg (1.81 mmol, 1.0 equiv.) of 2-(1,1-dimethylethyl)-4-methoxyphenol and 1.40 g (5.42 mmol, 3.0 equiv.) of 2',3-dimethoxy-4',5-dimethyl-2-hydroxybiphenyl. The current density was 2.8 mA/cm², the charge 2 F per 2-(1,1-dimethylethyl)-4-methoxyphenol (Q=350 C). After removal of the solvent, the reaction product was purified by column chromatography on silica gel 60 with a 9:1 (CH:EA) eluent mixture. The product was obtained as a yellow oil.

Yield: 126 mg (0.29 mmol, 8%)
GC (hard method, HP-5): $t_R$=22.69 min
$R_f$(Cy:EA=9:1)=0.51
$^1$H NMR (400 MHz, CDCl$_3$) δ [ppm]=1.45 (s, 9H, 7-H), 2.30 (s, 3H, 12-H), 2.31 (s, 3H, 10-H), 3.75 (s, 3H, 13-H), 3.91 (s, 3H, 11-H), 3.92 (s, 3H, 9-H), 5.58, 6.06 (bs, 2H, 8-H/14-H), 6.61 (d, 1H, 6''-H, $^4J_{6'',4''}$=1.2 Hz), 6.69 (d, 1H, 6-H, $^4J_{6,4}$=4 Hz), 6.71 (d, 1H, 4''-H, $^4J_{4',6'}$=1.2 Hz), 9.91 (d, 1H, 4-H, $^4J_{4,6}$=4 Hz), 6.95 (s, 1H, 3'-H), 7.22 (s, 1H, 6'-H).
$^{13}$C NMR (101 MHz, CDCl$_3$) δ [ppm]=20.38 (C-12), 21.24 (C-10), 29.84 (C-7), 35.30 (C-15), 55.82 (C-13), 56.15 (C-9), 56.35 (C-11), 110.75 (C-4''), 112.80 (C-6), 113.14 (C-3'), 113.98 (C-4), 123.70 (C-6''), 124.90 (C-1'), 126.98 (C-1), 127.36 (C-1''), 129.07 (C-5''), 131.60 (C-5'), 134.27 (C-6'), 138.41 (C-2'), 139.03 (C-3), 140.64 (C-2''), 146.35 (C-5), 146.64 (C-3''), 152.88 (C-2), 154.85 (C-4').
HRMS (ESI, pos. mode): m/z for C$_{27}$H$_{32}$O$_5$ (M+Na$^+$): calculated: 459.2147. found: 459.2147.

Example 4

2,2''-Dihydroxy-4'',5-dimethyl-2',3,4',5''-tetramethoxy[1,1';5',1'']terphenyl

The electrolysis was conducted according to GP1 with 250 mg (1.8 mmol, 1.0 equiv.) of 4-methoxy-3-methylphenol and 1.49 g (5.4 mmol, 3.0 equiv.) of 2-hydroxy-5-methyl-2',3,4'-trimethoxybiphenyl. The current density was 2.8 mA/cm², the charge 2 F per 4-methoxy-3-methylphenol (Q=350 C). First purification was effected by removing the reactants on a Kugelrohr still (120° C., $10^3$ mbar). The product was purified by column chromatography using silica gel 60 with a gradient of 4:1, then 7:3, then 2:1 (CH:EA). The terphenyl compound was obtained as a yellowish solid.

Yield: 126 mg (0.3 mmol, 17%)
GC (hard method, HP-5): $t_R$=23.54 min
$R_f$(Cy:EA=2:1)=0.14
$^1$H NMR (400 MHz, CDCl$_3$) δ [ppm]=2.25 (s, 3H), 2.34 (s, 3H), 3.79 (s, 3H), 3.93 (s, 3H), 3.93 (s, 3H), 3.97 (s, 3H), 5.57 (bs, 2H), 6.76-6.70 (m, 4H), 6.87 (s, 1H), 7.35 (s, 1H).
$^{13}$C NMR (101 MHz, CDCl$_3$) δ [ppm]=16.06, 21.22, 56.06, 56.09, 56.37, 56.66, 77.36, 96.56, 111.26, 112.87, 119.82, 119.93, 120.96, 123.04, 123.75, 124.46, 127.65, 129.24, 135.01, 141.03, 147.08, 152.09, 156.00, 157.29.
MS (ESI, pos. mode): m/z for C$_{24}$H$_{26}$O$_6$ (M+Na$^+$): calculated: 433.16. found: 433.16.

The inventive examples showed that the unsymmetric OCO pincer ligands can be prepared in satisfactory yields by the process according to the invention.

Example 5

Derivatization of the Phenol-Arene Component from Example 2 with Protecting Groups Protection with (1,1-dimethylethyl)dimethylsilyl chloride (TBDMS chloride)

Scheme 4: Reaction according to Example 5

A round-bottom flask with a drying tube was initially charged with 2.26 g of imidazole (33.2 mmol, 1.1 equ.). 8.29 g (30.2 mmol, 1.0 equ.) of the AB compound from Example 2 (2-hydroxy-5-methyl-2',3,4'-trimethoxybiphenyl) were dissolved in about 50 ml of dry dichloromethane and transferred into the flask. Subsequently, 5.92 g (39.3 mmol, 1.3 equ.) of TBDMS chloride were likewise dissolved in about 50 ml of dry dichloromethane and transferred into the flask. A further 100 ml of dichloromethane were added. The mixture was then stirred at room temperature for 24 h. During the reaction time, a colourless flaky precipitate formed. The product was isolated by means of extraction three times with 100 ml each time of water in order to remove the salt formed. After drying by means of sodium sulphate and removal of the dichloromethane on a rotary evaporator, the excess silyl chloride was removed by distillation (50° C., $10^{-3}$ mbar), in the course of which the product precipitated out as a colourless solid.

Yield: 98% (11.5 g, 29.6 mmol)
GC (hard method, HP-5): $t_R$=14.5 min
$R_f$ (CH:EA=5:1): 0.68
HRMS (ESI, pos. mode): m/z for CHO [M+Na$^+$]:
Calculated: 411.1968.
Found: 411.1960.
Melting point: 67.8° C.

$^1$H NMR (400 MHz, CDCl$_3$): δ [ppm]=−0.12 (s, 6H, 9, 10-H), 0.69 (s, 9H, 11-H, 12-H, 13-H), 2.30 (s, 3H, 8-H), 3.73 (s, 3H, 8'-H), 3.80 (s, 3H, 7'-H), 3.83 (s, 3H, 7-H), 6.50-6.53 (m, 2H, 3'-H, 5'-H), 6.65-6.68 (m, 1H, 4-H), 7.11-7.14 (m, 2H, 6-H, 6'-H)
$^{13}$C NMR (101 MHz, CDCl$_3$): δ [ppm]=−4.51 (C-9,C-10), 18.47 (C-14), 21.35 (C-8), 25.68 (C-11, C-12, C-13), 55.12 (C-8'), 55.55 (C-7'), 55.62 (C-7), 98.70 (C-3'), 103.95 (C-5'), 111.59 (C-4), 121.38 (C-1'), 124.12 (C-6), 129.91 (C-6'), 130.51 (C-1), 132.39 (C-5), 140.53 (C-2), 150.41 (C-3), 158.18 (C-4'), 160.31 (C-2')

Example 6

Derivatization of the Phenol-Arene Components from Example 2 with Protecting Groups Protection with tri(methylethyl)silyl chloride (TIPS chloride)

Scheme 5: Reaction according to Example 6

A round-bottom flask with a drying tube was initially charged with 5.27 g of imidazole (27.3 mmol, 2.5 equ.). 8.50 g (31.0 mmol, 1.0 equ.) of the AB compound from Example 2 (2-hydroxy-5-methyl-2',3,4'-trimethoxybiphenyl) were dissolved in about 60 ml of dry dichloromethane and transferred into the flask. Subsequently, 11.57 g (62.0 mmol, 2.0 equ.) of TIPS chloride were likewise added to the mixture, forming an orange/yellowish solution. The mixture was stirred at RT for 24 h. Subsequently, a further 0.5 equ. of TIPS chloride was added and the mixture was stirred at room temperature for a further 48 h. During the reaction time, a colourless flaky precipitate formed. The product was isolated by means of extraction three times with 100 ml each time of water in order to remove the salt formed. After drying by means of sodium sulphate and removal of the dichloromethane on a rotary evaporator, the excess silyl chloride was removed by distillation (50° C., $10^{-3}$ mbar), in the course of which the product precipitated out as a colourless solid.

Yield: 92% (13.3 g, 30.9 mmol)

GC (hard method, HP-5): $t_R$=15.8 min $R_f$ (CH:EA=5:1): 0.73

HRMS (ESI, pos. mode): m/z for CHO [M+Na$^+$]:

Calculated: 453.2437.

Found: 453.2423.

Melting point: 78.4° C.

$^1$H NMR (400 MHz, CDCl$_3$): δ [ppm]=0.87 (d, 18H, 9-H, 11-H, 12-H, 14-H, 15-H, 17-H), 1.56 (q, 3H, 10-H, 13-H, 16-H), 2.29 (s, 3H, 8-H), 3.70 (s, 3H, 8'-H), 3.78 (s, 3H, 7'-H), 3.83 (s, 3H, 7-H), 6.59-6.61 (m, 2H, 3'-H, 5'-H), 6.62-6.65 (m, 1H, 4-H), 7.09-7.12 (m, 2H, 6-H, 6'-H)

$^{13}$C NMR (101 MHz, CDCl$_3$): δ [ppm]=13.69 (C-8), 17.73 (C-9, C-11, C-12, C-14, C-15, C-17), 21.00 (C-10, C-13, C-16), 54.47 (C-8'), 55.08 (C-7'), 55.32 (C-7), 98.23 (C-3'), 103.48 (C-5'), 110.87 (C-4), 121.39 (C-1'), 123.61 (C-6), 128.81 (C-6'), 129.70 (C-1), 131.53 (C-5), 141.02 (C-2), 149.23 (C-3), 157.86 (C-4'), 159.93 (C-2')

Example 7

Preparation of 2,2''-dihydroxy-3''-(1,1-Dimethylethyl)-5-methyl-2',3,4',5''-tetramethoxy-[1,1',5',1'']-terphenyl The electrolysis was conducted according to the general procedure GP1 in a flange cell. For this purpose, an electrolyte volume of 33 ml of HFIP with 1.03 g of MTBS as conductive salt was used (0.09 M). For electrochemical cross-coupling, 0.90 g (5.0 mmol, 1.0 equ.) of 2-(1,1-dimethylethyl)-4-methoxyphenol and 6.45 g (15 mmol, 3.0 equ.) of the protected phenol-arene coupling product from Example 6 were used. The electrolysis was conducted in a galvanostatic manner, forming a deeply coloured solution. After the electrolysis had ended, the solvent was removed under reduced pressure on a rotary evaporator and the brown residue was filtered through silica gel 60 together with about 300 ml of ethyl acetate. The subsequent column chromatography separation (column measurements: 50×3 cm) of the product mixture through silica gel 60 as a flash chromatography was conducted twice with the following gradient in the eluent mixture: 95:5 to 9:1 to 5:1 to 2:1 (CH:EA, about 3 l of CH and 2 l of EA used per column). This afforded the corresponding product with the protecting group removed as a deep red solid.

Yield: 0.91 g of unprotected pincer ligands, (40%, 2.01 mmol)

GC (hard method, HP-5): $t_R$=22.34 min $R_f$ (CH:EA=5:1): 0.10

HRMS (ESI, pos. mode): m/z for CHO [M+Na$^+$]:

Calculated: 475.2097.

Found: 475.2103.

$^1$H NMR (400 MHz, CDCl$_3$): δ [ppm]=1.44 (s, 9H, 8''-H, 9''-H, 10''-H), 2.31 (s, 3H, 8-H), 3.75 (s, 3H, 11''-H), 3.91 (s, 3H, 8'-H), 3.91 (s, 3H, 7'-H) 3.93 (s, 3H, 7-H), 5.79 (s, 1H, 2''-H), 5.89 (s, 1H, 2-H), 6.65 (d, 1H, 3'-H), 6.67-6.72 (m, 3H, 4-H, 6-H, 6''-H), 6.91 (d, 1H, 4''-H), 7.30 (s, 1H, 6'-H)

$^{13}$C NMR (101 MHz, CDCl$_3$): δ [ppm]=20.90 (C-8), 29.51 (C-8'', C-9'', C-10''), 34.98 (C-7''), 55.50 (C-11''), 55.86 (C-8'), 56.16 (C-7'), 56.32 (C-7), 96.27 (C-3'), 111.04 (C-6''), 112.42 (C-4''), 113.59 (C-4), 119.79 (C-5'), 120.65 (C-1'), 123.49 (C-6), 124.20 (C-1), 126.59 (C-1''), 129.02 (C-6'), 135.15 (C-5), 138.61 (C-3''), 140.72 (C-2''), 146.22 (C-3), 146.84 (C-2), 152.55 (C-5''), 156.03 (C-2'), 157.13 (C-4')

Example 8

Preparation of 2,2''-dihydroxy-4'',5-dimethyl-2',3,4',5''-tetramethoxy-[1,1',5',1'']-terphenyl The electrolysis was conducted according to the general procedure GP1 in a flange cell. For this purpose, an electrolyte volume of 33 ml of HFIP with 1.03 g of MTBS as conductive salt was used (0.09 M). For electrochemical cross-coupling, 0.69 g (5.0 mmol, 1.0 equ.) of 4-methoxy-3-methylphenol and 6.45 g (15 mmol, 3.0 equ.) of the protected phenol-arene coupling product from Example 6 were used. The electrolysis was galvanostatic, forming a black solution. After the electrolysis had ended, the solvent was removed under reduced pressure on a rotary evaporator and the brown solution that remained was filtered through silica gel 60 together with about 300 ml of ethyl acetate. The subsequent column chromatography separation (column measurements: 50×3 cm) of the product mixture through silica gel 60 as a flash chromatography was conducted twice with the following gradient in the eluent mixture: 95:5 to 9:1 to 5:1 to 2:1 (CH:EA, about 3 l of CH and 2 l of EA used per column). This afforded the corresponding product with the protecting group removed as a deep red solid.

Yield: 0.88 g of unprotected pincer ligands, (43%, 2.15 mmol)

GC (hard method, HP-5): $t_R$=20.3 min $R_f$ (CH:EA=5:1): 0.1

HRMS (ESI, pos. mode): m/z for CHO [M+H$^+$]:
Calculated: 411.1802.
Found: 411.1797.

$^1$H NMR (400 MHz, CDCl$_3$): δ [ppm]=2.22 (s, 3H, 7'-H'), 2.31 (s, 3H, 8-H), 3.76 (s, 3H, 8"-H), 3.91 (s, 3H, 8'-H), 3.91 (s, 3H, 7'-H), 3.96 (s, 3H, 7-H), 5.79 (s, 1H, 2"-H), 5.93 (bs, 1H, 2-H), 6.67-6.74 (m, 3'-H, 4-H, 6-H, 6"-H), 6.83 (s, 1H, 3"-H), 7.31 (s, 1H, 6'-H)

$^{13}$C NMR (101 MHz, CDCl3): δ [ppm]=15.79 (C-7"), 20.99 (C-8), 55.83 (C-8"), 55.85 (C-8'), 56.15 (C-2'), 56.44 (C-7), 96.26 (C-3'), 110.99 (C-4), 112.62 (C-6"), 119.62 (C-3"), 120.69 (C-4"), 122.17 (C-5'), 123.37 (C-1'), 124.15 (C-6), 127.43 (C-1"), 129.03 (C-1), 134.79 (C-6'), 140.77 (C-5), 146.84 (C-2"), 151.88 (C-5"), 155.75 (C-3), 157.05 (C-2), 158.29 (C-4'), 158.43 (C-2')

As Examples 7 and 8 show, it was possible to further increase the yield of m-terphenyl compound by the introduction of a protecting group (silyl group) into the phenol-arene coupling product in the subsequent coupling in process step c) conducted by electrochemical means (two- to threefold increase in yield). In this way, it is thus possible to distinctly increase the efficiency of the overall process.

The invention claimed is:

1. A process for preparing unsymmetric compounds from the group of the m-terphenyls, comprising the process steps of
    a) reacting a first substituted or unsubstituted phenol with a 1,3-disubstituted arene which may be substituted in the 2 and 5 positions to obtain a phenol-arene coupling product and
    b) optionally protecting the OH group of the phenol-arene coupling product with a protecting group to obtain a protected phenol-arene coupling product,
    c) reacting the phenol-arene coupling product from a) or b) with a second substituted or unsubstituted phenol to obtain an unsymmetric m-terphenyl,
    with the proviso that the first phenol and the second phenol have different substitution, wherein
    at least one of process steps a) and c) is conducted as an electrochemical process step, and the electrochemical process step comprises:
    mixing at least one solvent and at least one conductive salt to form a mixture;
    adding compounds to be converted to the mixture to form a reaction mixture:
    introducing at least two electrodes into the reaction mixture; and
    applying a voltage to the electrodes.

2. The process according to claim 1, wherein both process steps a) and c) are conducted as electrochemical process steps.

3. The process according to claim 1, wherein the electrochemical process step further comprises:
    adding the phenol in molar deficiency relative to the other component to be converted,
    converting the components to the corresponding coupling products,
    switching off the voltage, and optionally
    isolating and/or purifying the reaction product.

4. The process according to claim 1, wherein the molar ratio of the 1,3-disubstituted arene which may be substituted in the 2 and 5 positions to the first substituted or unsubstituted phenol is in the range from 1.5:1 to 6:1.

5. The process according to claim 1, wherein the molar ratio of the phenol-arene coupling product to the second phenol is in the range from 1.5:1 to 6:1.

6. The process according to claim 1, wherein the first substituted or unsubstituted phenol corresponds to the formula (A)

(A)

the second substituted or unsubstituted phenol to the formula (A')

(A')

and the 1,3-disubstituted arene which may be substituted in the 2 and 5 positions to the formula (B)

(B)

and $R^1$, $R^2$, $R^3$, $R^4$, $R^5$, $R^6$, $R^7$, $R^8$, $R^{10}$ and $R^{12}$ are each independently selected from the group consisting of hydrogen, $(C_1\text{-}C_{12})$-alkyl, O—$(C_1\text{-}C_{12})$-alkyl, $(C_6\text{-}C_{20})$-aryl, O—$(C_6\text{-}C_{20})$-aryl and halogen, in which $R^9$ and $R^{11}$ are each independently selected from the group consisting of $(C_1\text{-}C_{12})$-alkyl, O—$(C_1\text{-}C_{12})$-alkyl, $(C_6\text{-}C_{20})$-aryl, O—$(C_6\text{-}C_{20})$-aryl and halogen, and in which at least one pair among the $R^1/R^5$, $R^2/R^6$, $R^3/R^7$ and $R^4/R^8$ pairs consists of different radicals.

7. The process according to claim 6, where $R^{10}$ and $R^{12}$ are identical.

8. The process according to claim 1, wherein the at least one solvent is selected from the group consisting of acetonitrile, propylene carbonate, methyl carbonate, nitromethane, ethylene glycol dimethyl ether, methanesulphonic acid, benzene, toluene, water, methanol, ethanol, propanol, isopropanol, halogenated solvents, halogenated or non-halogenated acids, and mixtures thereof.

9. The process according to claim 8, wherein the solvent is methanol, formic acid, trifluoroacetic acid, hexafluoroisopropanol or mixtures thereof.

10. The process according to claim 1, wherein the reaction is conducted without the use of organic oxidizing agents.

11. The process according to claim 1, wherein the at least one conductive salt is selected from the group consisting of tetra($C_1$-$C_6$-alkyl)ammonium and 1,3-di($C_1$-$C_6$-alkyl)imidazolium salts, with the proviso that the alkyl groups may be halogen-substituted.

12. The process according to claim 11, wherein the counterions of the conductive salts are selected from the group consisting of arsenate, sulphate, hydrogensulphate, alkylsulphate, alkylphosphate, perchlorate, fluoride, arylsulphate, hexafluorophosphate, and tetrafluoroborate.

13. The process according to claim 1, wherein the conductive salt is selected from the group consisting of quaternary ammonium borates, ammonium fluoroalkylphosphates, ammonium fluoroalkylarsenates, ammonium trifluoromethylsulphonates, ammonium bis(fluoromethanesulphon)imides, ammonium tris(fluoromethanesulphonyl)methides, methyltributylammonium methylsulphate, methyltriethylammonium methylsulphate, tetrabutylammonium hexafluorophosphate, tetraethylammonium tetrafluoroborate, lithium hexafluorophosphate, and tetraethylammonium tetrafluoroborate.

14. The process of claim 4, wherein the molar ratio of the 1,3-disubstituted arene which may be substituted in the 2 and 5 positions to the first substituted or unsubstituted phenol is in the range from 2:1 to 3:1.

15. The process of claim 5, wherein molar ratio of the phenol-arene coupling product to the second phenol is in the range from 2:1 to 3:1.

16. The process of claim 6, wherein $R^1$, $R^2$, $R^3$, $R^4$, $R^5$, $R^6$, $R^7$, $R^8$, $R^{10}$ and $R^{12}$ are each independently selected from the group consisting of hydrogen, $(C_1\text{-}C_{12})$-alkyl, O—$(C_1\text{-}C_{12})$-alkyl and halogen.

17. The process of claim 16, wherein $R^1$, $R^2$, $R^3$, $R^4$, $R^5$, $R^6$, $R^7$, $R^8$, $R^{10}$ and $R^{12}$ are each independently selected from the group consisting of hydrogen, $(C_1\text{-}C_{12})$-alkyl, and O—$(C_1\text{-}C_{12})$-alkyl.

18. The process of claim 6, wherein $R^9$ and $R^{11}$ are each independently selected from the group consisting of $(C_1\text{-}C_{12})$-alkyl, O—$(C_1\text{-}C_{12})$-alkyl, and halogen.

19. The process of claim 18, wherein $R^9$ and $R^{11}$ are each independently selected from $(C_1\text{-}C_{12})$-alkyl or O—$(C_1\text{-}C_{12})$-alkyl.

20. The process of claim 7, wherein $R^{10}$ and $R^{12}$ are hydrogen.

21. The process of claim 9, wherein the solvent is methanol, hexafluoroisopropanol, or mixtures thereof.

22. The process of claim 21, wherein the solvent is hexafluoroisopropanol.

23. The process of claim 13, wherein the conductive salt is methyltriethylammonium methylsulphate or methyltributylammonium methylsulphate.

24. The process of claim 23, wherein the conductive salt is methyltributylammonium methylsulphate.

* * * * *